United States Patent [19]

Shimizu et al.

[11] Patent Number: 4,908,473

[45] Date of Patent: Mar. 13, 1990

[54] PROCESS FOR SELECTIVELY HYDROESTERIFYING DIOLEFIN

[75] Inventors: Isoo Shimizu; Yasuo Matsumura, both of Yokohama; Yutaka Arai, Tokyo, all of Japan

[73] Assignee: Nippon Petrochemicals Company, Limited, Tokyo, Japan

[21] Appl. No.: 275,081

[22] PCT Filed: Mar. 12, 1988

[86] PCT No.: PCT/JP88/00264

§ 371 Date: Nov. 14, 1988

§ 102(e) Date: Nov. 14, 1988

[87] PCT Pub. No.: WO88/07034

PCT Pub. Date: Sep. 22, 1988

[30] Foreign Application Priority Data

Mar. 12, 1987 [JP] Japan .................................. 62-57099

[51] Int. Cl.$^4$ ............................................. C07C 69/76
[52] U.S. Cl. ...................................... 560/104; 562/406
[58] Field of Search ......................... 560/104; 562/406

[56] References Cited

U.S. PATENT DOCUMENTS 4,172,087  10/1979  Knifton .............................. 562/406
4,257,973  3/1981   Mrowca ............................. 562/406
4,786,443  11/1988  Drent et al. ....................... 562/406

Primary Examiner—Paul J. Killos
Attorney, Agent, or Firm—Scully, Scott, Murphy & Presser

[57] ABSTRACT

A process for selectively hydroesterifying a diolefin, which comprises reacting a (1-arylethenyl)vinylbenzene with carbon monoxide and water or a lower alcohol at a reaction temperature of 40° to 200° C. and a carbon monoxide pressure 20 to 700 kg/cm$^2$ in the presence of a noble metal complex catalyst to thereby selectively hydroesterifying only the vinyl group of it and produce α-((1-arylethenyl)phenyl)propionic acid or its alkyl ester. The starting material to be hydroesterified may be a mixture of 1,1-di(substituted aryl)ethylene not substituted by a vinyl group.

8 Claims, No Drawings

PROCESS FOR SELECTIVELY HYDROESTERIFYING DIOLEFIN

DESCRIPTION

1. Technical Field

This invention relates to a process for selective hydroesterification. More particularly, the invention relates to a process for producing unsaturated acid or its ester by selectively hydroesterifying diolefin.

Furthermore, the invention relates to a process for selectively hydroesterifying only diolefin in a material which contains certain monoolefins.

2. Background Art

The methods of carbonylation of olefin by carbon monoxide are employed widely in industry, for example, in connection with monoolefins. Furthermore, for example, in U.S. Pat. No. 4,329,507, it is disclosed that ketoprofen (antiphlogistic agent, trade name) is obtained in a high yield by reacting 3-vinylbenzophenone with carbon monoxide in dilute hydrochloric acid in the presence of a catalyst of palladium.

However, with regard to diolefins, such instance is few. For example, in Japanese Laid-Open Patent Publication Nos. 58-210033 and 59-110643, 5-ethylidene bicyclo[2.2.1]heptene-2 is carbonated and its two unsaturated groups are carbonylated. In the same references, only one unsaturated group is carbonylated by regulating the feed quantities of hydrogen and carbon monoxide.

The inventors of the present application have found out that, with regard to diolefin having specific structure, when it is reacted with carbon monoxide and water or alcohol, only one unsaturated groups is carbonylated, thereby accomplishing the present invention.

DISCLOSURE OF INVENTION

That is, the present invention relates to a process for selective hydroesterification which is characterized in that (1-arylethenyl)vinylbenzene represented by the following formula (I) is reacted with carbon monoxide and water or an alcohol at a reaction temperature of 40°–200° C. and a carbon monoxide pressure of 20 to 700 kg/cm² in the presence of a noble metal complex carbonylation catalyst to prepare α-((1-arylethenyl)-phenyl)propionic acid or its alkyl ester represented by the following formula (II)

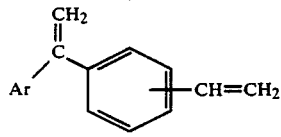

Formula (I)

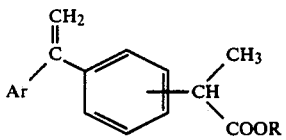

Formula (II)

wherein Ar is an aryl group which can have a substituent group except vinyl group and R is a hydrogen atom or a lower alkyl group.

The present invention is described in more detail in the following.

The aryl group Ar in the above (1-arylethenyl)vinylbenzene is exemplified by aryl groups such as phenyl, alkylphenyl, alkoxyphenyl, phenoxyphenyl and biphenyl groups as well as aryl groups in which various other substituent groups except vinyl group are introduced to phenyl groups. As such substituent groups for the aryl group, carboxyl group, hydroxyl group, alkoxy group, nitro group and alkoxycarbonyl group are exemplified.

More particularly, the above (1-arylethenyl)vinylbenzenes are exemplified those having aryl groups of phenyl, tolyl, xylyl or the like, such as (1-phenyletenyl)-vinylbenzene, (1-tolylethenyl)vinylbenzene, (1-xylylethenyl)vinylbenzene, and (1-ethylphenylethenyl)vinylbenzene, having phenyl, tolyl or xylyl as the aryl group as well as (1-hydroxyphenylethenyl)vinylbenzene, (1-methoxyphenylethenyl)vinylbenzene, (1-dimethoxyphenylethenyl)vinylbenzene, (1-ethoxyphenylethenyl)-vinylbenzene, (1-carboxyphenylethenyl)vinylbenzene, (1-methoxycarbonylphenylethenyl)vinylbenzene, (1-di(methoxycarbonyl)phenylethenyl)vinylbenzene, (1-ethoxycarbonylphenylethenyl)vinylbenzene and (1-nitrophenylethenyl)vinylbenzene.

In the above compounds, all position isomers in view of the positions of substituent groups are included, however, m-isomers are preferable.

According to the method of the present invention, the compound of the formula (II) is produced by selectively hydroesterifying the vinyl group.

By the hydroesterification according to the present invention, only the vinyl group is carbonylated selectively in the compound of the foregoing formula (I) and the ethenyl group having the aryl groups does not react substantially under the foregoing reaction conditions of the present invention. Incidentally, in the case that the ethenyl group has an alkyl group in place of the aryl group, any of double bonds are hydroesterified.

The compounds produced by the reaction of the present invention are those in which a hydrogen atom and a carboxyl group or alkoxycarbonyl group are added to the vinyl group of the compound of the foregoing formula (I). Especially, the position of the addition of carboxyl group or alkoxycarbonyl group is generally the α-position in the vinyl group.

Therefore, the compounds which are produced by the method of the present invention correspond to the foregoing compounds such as α-((1-phenylethenyl)-phenyl)propionic acid, α-((1-tolylethenyl)phenyl)propionic acid, α-((1-xylylethenyl)phenyl)propionic acid, α-((1-ethylphenylethenyl)phenyl)propionic acid, α-((1-hydroxyphenylethenyl)phenyl)propionic acid, α-((1-methoxyphenylethenyl)phenyl)propionic acid, α-((1-dimethoxyphenylethenyl)phenyl)propionic acid, α-((1-ethoxyphenylethenyl)phenyl)propionic acid, α-((1-carboxyphenylethenyl)phenyl)propionic acid, α-((1-methoxycarbonylphenylethenyl)phenyl)propionic acid, α-((1-di(methoxycarbonyl)phenylethenyl)phenyl)propionic acid α-((1-ethoxycarbonylphenylethenyl)-phenyl)propionic acid and α-((1-nitrophenylethenyl)-phenyl)propionic acid.

The noble metal complex catalysts to be used for the above carbonylation are noble metal complexes of Pd, Rh and Ir, and preferably, the complex of Pd. As the noble metals, those having halogen atoms, trivalent phosphorus compounds, or having ligands of carbon monoxide as carbonyl complex are used. As the noble metals, such as palladium, those having oxidation number of 0 to 2 can be used.

The catalysts are exemplified by bistriphenylphosphine dichloropalladium, bistributylphosphine dichloropalladium, bistricyclohexylphosphine dichloropalladium, π-allyltriphenylphosphine dichloropalladium, triphenylphosphine piperidine dichloropalladium, bisbenzonitrile dichloropalladium, biscyclohexyloxime dichloropalladium, 1,5,9-cyclodecatriene dichloropalladium, bistriphenylphosphine dicarbonylpalladium, bistriphenylphosphine palladium acetate, bistriphenylphosphine palladium dinitrate, bistriphenylphosphine palladium sulfate, and tetrakistriphenylphosphine palladium.

The catalyst can be used in the form of complex by adding the complex in the reaction system. Furthermore, it is also possible to form a complex in the reaction system by adding ligands separately into the reaction system.

The use quantity of the catalyst is 0.0001–0.5 mole, preferably 0.001–0.1 mole, to 1 mole of (1-arylethenyl)-vinylbenzene of the formula (I). When the compound which produces a complex is used, the addition quantity of the compound is 0.8–10 moles, preferably 1–4 moles, to 1 mole of the noble metal such as Pd, Rh or Ir as the nuclei of complex.

The carbonylation is carried out at 40°–200° C. preferably 70°–150° C., in reaction temperature, 20–700 kg/cm², preferably 40–500 kg/cm², in reaction pressure. Furthermore, it is possible to add an acid such as hydrogen chloride or boron trifluoride in order to promote the reaction.

If the reaction temperature is below 40° C., the rate of reaction is very low which is not acceptable in practice. On the other hand, at carbonylation temperature of above 200° C., it is not desirable that the vinyl group is carbonylated and the internal olefin-type carbon-carbon double bond is also carbonylated. In addition, side reactions such as polymerization, addition of water or alcohol and decomposition of complex catalyst are caused to occur undesirably.

In connection with the pressure of carbon monoxide, if the pressure is 20 kg/cm² or higher, a practically workable rate of reaction can be obtained. However, the pressure above 700 kg/cm² is not desirable because there is possibility to cause the carbonylation to vinyl group as well as the carbonylation to internal olefin-type carbon-carbon double bond.

The alcohols used for the hydroesterification are lower alcohols such as methyl alcohol and ethyl alcohol. Methyl alcohol is preferable in view of reactivity.

The hydroesterification reaction is continued until the lowering of pressure owing to the absorption of carbon monoxide is not observed in the coexistence of water or alcohol. The reaction time of 4 to 20 hours is generally sufficient. Furthermore, it is sufficient that carbon monoxide in pure form is fed, however, any gas which is inert to the hydroesterification can coexist.

In the hydroesterification in the coexistence of water, the aimed α-((1-arylethenyl)phenyl)propionic acid is directly produced. In this case, it is sometimes preferable to use a solvent such as acetone, tetrahydrofuran or dioxane which is water-soluble and which does not exert inhibitory effect to the hydroesterification.

In the hydroesterification in the coexistence of a lower alcohol, an alkyl ester of α-((1-arylethenyl)-phenyl)propionic acid is produced. This ester can be converted easily into α-((1-arylethenyl)phenyl)propionic acid by ordinary hydrolysis. More particularly, the former is heated with an aqueous solution of sodium hydroxide and then it is acidified with hydrochloric acid or sulfuric acid and the free carboxylic acid is then extracted with an organic solvent.

After the carbonylation, the reaction product is subjected to separation by distillation or recrystallization and the aimed compound of α-((1-arylethenyl)phenyl)-propionic acid or its alkyl ester (formula II) and catalyst can be separated quite easily. The recovered complex catalyst can be used again.

In the present invention, (1-arylethenyl)vinylbenzene of the foregoing formula (I) as the starting material can be the one which is contaminated with 1,1-di(substituted aryl)ethylene which is represented by the following formula (III).

(III)

(in which Ar₁ and Ar₂ are the same or different substituted aryl groups and their substituent groups can be replaced by radicals other than vinyl group.)

That is, it was found out by the present inventors that 1,1-di(substituted aryl)ethylene of the above formula (III) is not hydroesterified substantially under the conditions to hydroesterify the vinyl group of (1-arylethenyl)vinylbenzene of the formula (I) of the present invention.

Accordingly, the starting material used for the hydroesterification of the present invention can be a mixture containing 1,1-di(substituted aryl)ethylene of the above formula (III), which provides an advantage that refining process can be omitted.

The 1,1-di(substituted aryl)ethylene of the above formula (III) is a compound in which two substituted aryl groups are connected to the same carbon atom in the ethylene moiety.

The substituted aryl group herein referred to means an aromatic group which may have a substituent group or groups other than vinyl group. It is exemplified by phenyl group and naphthyl group having no substituent group as well as aryl groups having alkyl groups, alkoxy groups, aryloxy groups or the like.

Such 1,1-di(substituted aryl)ethylenes are exemplified by 1,1-diphenylethylene having no substituent group, and substituted 1,1-diphenylethylenes in which the substituted aryl groups are alkylphenyls such as methylphenyl, dimethylphenyl, ethylphenyl, methylethylphenyl, propylphenyl, diethylphenyl and butylphenyl; alkoxyphenyl groups in which the substituted aryl groups such as methoxyphenyl, dimethoxyphenyl, ethoxyphenyl, propoxyphenyl and butoxyphenyl; non-condensed polycyclic aryl groups such as phenylphenyl group, phenoxyphenyl group and benzoylphenyl group; condensed polycyclic aryl groups of alkylnaphthyl groups such as methylnaphthyl, dimethylnaphthyl and ethylnaphthyl and alkoxynaphthyl groups such as methoxynaphthyl, dimethoxynaphthyl and ethoxynaphthyl.

As described in the foregoing passages, the mixture of (1-arylethenyl)vinylbenzene of the foregoing formula (I) and 1,1-di(substituted aryl)ethylene of the foregoing formula (III) can be used as the starting material for the hydroesterification.

In an embodiment of the invention to use a preferable material as a mixture, 1-phenyl-1-ethylphenyl-ethane is dehydrogenated and the dehydrogenation product from this dehydrogenation step is hydroesterified.

That is, this method consists of the following dehydrogenation step (I) and hydroesterification step (II).

Step (I):

In this process, 1-phenyl-1-ethylphenyl-ethane is brought into contact with iron oxide and/or chromium oxide dehydrogenation catalyst at a temperature of 400° C. to 650° C. in the presence of an inert gas to obtain 1-phenyl-1-ethylphenyl-ethylene represented by the formula (B) and 1-phenyl-1-vinylphenyl-ethylene represented by the formula (C), and Step (II):

the dehydrogenation product containing at least 1-phenyl-1-ethylphenyl-ethylene represented by the formula (B) and 1-phenyl-1-vinylphenyl-ethylene represented by the formula (C) obtained in Step (I) is hydroesterified with carbon monoxide and water or alcohol in the presence of a noble metal complex carbonylation catalyst at 40°-200° C. in reaction temperature and 20-700 kg/cm² in reaction pressure, thereby selectively hydroesterifying 1-phenyl-1-vinylphenyl-ethylene represented by the formula (C).

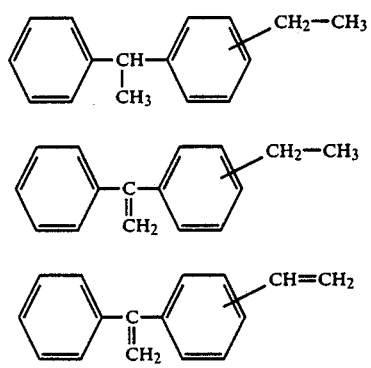

The above Step (I) is a process to convert 1-phenyl-1-ethylphenyl-ethane mainly into 1-phenyl-1-ethylphenyl-ethylene and 1-phenyl-1-vinylphenyl-ethylene by dehydrogenating with a dehydrogenation catalyst.

The dehydrogenation catalyst used in the dehydrogenation step (I) is iron oxide catalyst, chromium oxide catalyst or a mixed catalyst of these oxides. This catalyst contains the main components of iron oxide, chromium oxide or the mixture of these oxides and it can contain suitable promoters of the oxide of molybdenum, vanadium, manganese, zinc, copper or the like. Furthermore, the oxide of alkali metal or alkaline earth metal such as sodium, potassium, magnesium, calcium or barium can be added in order to improve the efficiency of dehydrogenation. The form of these catalysts may be the one which is mainly composed of iron oxide or chromium oxide itself or carrier-supported catalyst which is supported on a carrier of, for example, alumina, silica-alumina or silica.

The above dehydrogenation step (I) is carried out by diluting with an inert gas. This inert gas may be properly selected from those which do not inhibit the dehydrogenation reaction and which exert no inhibitory effect as catalyst poison. The inert gases are exemplified by inorganic gases such as nitrogen, hydrogen, helium, argon and steam and organic gas such as methane. Among them, steam is a preferable diluent in view of practical handling.

The dilution with an inert gas is preferably done with over ten times by mole of an inert gas relative to 1-phenyl-1-ethylphenyl-ethane. When the rate of dilution is too low, it is not efficient because the efficiency of dehydrogenation is lowered as well as the life of catalyst is shortened owing to the occurrence of coking. Even though the inert gas in a large ratio is effective, the upper limit of its molar ratio relative to 1-phenyl-1-ethylphenyl-ethane is practically about 500.

The quantity of feed of 1-phenyl-1-ethylphenyl-ethane relative to the unit weight of catalyst is preferably 0.1 to 5 times by weight per hour. The feed quantity which is smaller than this value is not desirable because the starting material of 1-phenyl-1-ethylphenyl-ethane is decomposed and the demethylation in the portion of ethyl group connected to two aryl groups is caused to occur. Furthermore, when the feed quantity exceeds 5 times by weight, the reaction is not effective because the efficiency of dehydrogenation is too low.

The temperature of contact with the dehydrogenation catalyst is preferably in the range of 400° C. to 650° C., and more preferably in the range of 500° C. to 600° C. At temperatures below 400° C., the dehydrogenation efficiency is low and it is not practically acceptable. On the other hand, at temperatures above 650° C., the decomposition and demethylation of 1-phenyl-1-ethylphenyl-ethane itself become serious, which are not desirable.

The dehydrogenation pressure is preferably a reduced pressure in view of the equilibrium in dehydrogenation and it is generally from a reduced pressure to about 10 kg/cm².

In the dehydrogenation step (I), 1-phenyl-1-ethylphenyl-ethane is dehydrogenated under the above conditions to dehydrogenate and to convert it mainly into 1-phenyl-1-ethylphenyl-ethylene and 1-phenyl-1-vinylphenyl-ethylene. In other words, the starting material of 1-phenyl-1-ethylphenyl-ethane is converted into a monoolefin of 1-phenyl-1-ethylphenyl-ethylene of the formula (B) in which the ethane moiety having two aryl groups is converted into ethylene, and into a diolefin of 1-phenyl-1-vinylphenyl-ethylene of the formula (C) in which both the two ethyl moieties in 1-phenyl-1-ethylphenyl-ethane are converted. Furthermore, a monoolefin of 1-vinylphenyl-1-phenyl-ethane is also by-produced in small quantity as a dehydrogenation product in which the ethyl group on the phenyl group is converted into vinyl group. It is difficult to separate this compound from the dehydrogenation product by means of ordinary distillation operation, however, it causes substantially no trouble because the produced quantity of the compound is very small in the method of the present invention. In other words, the reaction product can be fed to the next Step (II) without removing it.

Even though it depends upon the efficiency of dehydrogenation, the starting material of unreacted 1-phenyl-1-ethylphenyl-ethane is also taken out This can be also used intact for the next step (II) without any disadvantage.

The dehydrogenation product obtained from the foregoing step (I) is subjected to an ordinary industrial separation process, for example, separation by distillation, to recover a fraction containing 1-phenyl-1-ethylphenyl-ethylene and 1-phenyl-1-vinylphenyl-ethylene and it is fed to the next step. Because the boiling points of 1-phenyl-1-ethylphenyl-ethylene and 1-phenyl-1-vinylphenyl-ethylene obtained in the step (I) are close to each other and the boiling point of the starting material of 1-phenyl-1-ethylphenyl-ethane is also close, the separation of them by means of industrial separation method such as ordinary distillation is difficult. Therefore, as far as the separation is done by industrial operation, it cannot be avoided that the fraction fed to the next step contains at least 1-phenyl-1-ethylphenyl-ethylene and 1-phenyl-1-vinylphenyl-ethylene together. Furthermore, the dehydrogenation catalyst of the present invention is a desirable one because it has quite a high efficiency of dehydrogenation relative to the starting material. However, as described above, the catalyst has a defect that the formation of two kinds of unsaturated hydrocarbons which are similar in molecular weights and chemical structures cannot be avoided.

However, in the present invention, it is not necessary to separate the respective reaction products of the step (I) when they are fed to the step (II) from the step (I). It is practically impossible to separate the monoolefin of the formula (B), the diolefin of the formula (C) and the starting material of 1-phenyl-1-ethylphenyl-ethane of the formula (A) into respective components. Even though it is not necessary that the reaction product is refined, if desired, lighter decomposition products and heavier polymeric substances which are by-produced in the step (I) can be separated. Therefore, the present invention is characterized in that the reaction product of the step (I) can be fed to the next step (II) by subjecting it to a simple industrial operation of distillation. The raw material for the step (II) is a fraction in the boiling range of 80°–170° C., preferably 90°–160° C. at a reduced pressure of 2–3 mm Hg.

In the hydroesterification of the step (II) of the present invention, the reactants containing at least 1-phenyl-1-ethylphenyl-ethylene and 1-phenyl-1-vinylphenyl-ethylene obtained in the step (I) are hydroesterified with carbon monoxide and water or alcohol. The positions of substituent groups are maintained as they stand in the hydroesterification products.

The alcohols are exemplified by lower alcohols having 1 to 4 carbon atoms such as methanol, ethanol, propanol, isopropanol and butanol. Alcohols having 5 or more carbon atoms are not desirable because the rate of hydroesterification is lowered. A preferable alcohol is methanol.

By the hydroesterification of the step (II), 1-phenyl-1-ethylphenyl-ethane of the formula (A) and 1-phenyl-1-ethylphenyl-ethylene of the formula (B) contained in the mixture obtained in the step (I) are not changed substantially in this hydroesterification but 1-phenyl-1-vinylphenyl-ethylene of the formula (C) is converted into the aimed product of [(1-phenylethenyl)phenyl]-propionic acid and/or its ester. This aimed product of (1-phenylethenyl)phenyl]propionic acid can be separated easily from 1-phenyl-1-ethylphenyl-ethane of the formula (A) and 1-phenyl-1-ethylphenyl-ethane of the formula (B) in the hydroesterification product with water, by a method such as extraction with an aqueous alkaline solution. Furthermore, alkyl esters of [(1-phenylethenyl)phenyl]propionic acid as the reaction product with alcohols are also easily separated an ordinary separation method such as distillation operation. Accordingly, it is easy to refine the aimed product and it is possible to obtain the aimed product in high purity. In addition, 1-phenyl-1-ethylphenyl-ethane of the formula (A) and 1-phenyl-1-ethylphenyl-ethylene of the formula (B) which are separated from the mixture obtained in the step (II) can be used as the starting materials for the step (I).

α-[m-(1-Phenylethenyl)phenyl]propionic acid and/or its alkyl ester as the position isomer of [(1-phenylethenyl)phenyl]propionic acid or its ester obtained by the method of the present invention, can be easily converted into the antiphlogistic agent of the trade name: ketoprofen, by oxidizing the former, or hydrolyzing and then oxidizing or oxidizing and then hydrolyzing it.

Meanwhile, as the starting material of 1-phenyl-1-ethylphenyl-ethane in the foregoing dehydrogenation step (I), it is desirable that a fraction containing 1-phenyl-1-(3-ethylphenyl)ethane (hereinafter referred to as PEPE) is used, which fraction is recovered from a heavy fraction that is by-produced in the process of alkylation of benzene with ethylene in the presence of an alkylation catalyst. This material for dehydrogenation is described in the following.

In order to prepare a raw material for styrene monomer by dehydrogenation for producing polystyrene, it is widely carried out in industry that benzene is alkylated with ethylene to prepare ethylbenzene.

In the preparation of ethylbenzene, benzene is firstly alkylated with ethylene in the presence of an alkylation catalyst to obtain an alkylation product mainly containing unreacted benzene, ethylbenzene, polyethylbenzene and heavier products. This can be done by known methods of ethylbenzene preparation such as liquid phase alkylation method and gas phase alkylation method. The molar ratio of benzene to ethylene can be about 25:1 to 2:1, preferably about 10:1 to 3:1. In the liquid phase reaction, the alkylation catalysts are exemplified by Friedel-Crafts catalysts such as organic aluminum halides, aluminum chloride and aluminum bromide; Lewis acids such as $ZnCl_2$, $FeCl_3$ and $BF_3$ containing a promoter; and Brønsted acids including sulfuric acid, sulfonic acid and p-toluenesulfonic acid. Benzene is reacted with ethylene in a temperature range of about 0°–175° C., preferably about 20°–150° C., in the presence of an alkylation catalyst of about 0.002–0.050 part by weight, preferably about 0.005–0.030 part by weight relative to ethylbenzene to be produced. When the reaction temperature is lower than 0° C., the yield of ethylbenzene is lowered. On the other hand, when the temperature is above 175° C., the yield of ethylbenzene is lowered due to side reaction, which is not desirable. With regard to the reaction pressure, a higher pressure is desirable in order to facilitate the dissolution of ethylene, however, the pressure up to 100 $kg/cm^2$ is practically employed. The duration of reaction is generally 10 minutes to 10 hours, preferably about 20 minutes to 3 hours.

In the gas phase alkylation method, the alkylation materials are brought into contact with an appropriate alkylation catalyst containing diatomaceous earth, silica or alumina, or aluminum silicate carrying phosphoric acid, or synthetic zeolite catalyst such as ZSM-5 type synthetic zeolite, at a temperature in the range of about 250°–450° C., preferably about 300°–400° C., and a pressure in the range of about 28–85 $kg/cm^2$, preferably about 42–70 $kg/cm^2$, at an ordinary space velocity.

As a result of the alkylation, alkylation products of unreacted benzene, aimed ethylbenzene, polyethylbenzene and heavier product containing PEPE are obtained. If desired, the contained alkylation catalyst is removed from the alkylation products. For example, when aluminum chloride is used as an alkylation catalyst, the alkylation products are fed to a settler, in which the aluminum chloride is precipitated and removed. If necessary, the removed catalyst is recycled to the reaction system. The remaining alkylation products are then rinsed with water and neutralized.

Then, a fraction containing PEPE (hereinafter referred to as dehydrogenation raw material fraction of the present invention) is recovered from the above alkylation products mainly containing unreacted benzene, aimed ethylbenzene, polyethylbenzene and heavier product containing PEPE.

In this recovery process, the alkylation products is distilled under atmospheric pressure or a reduced pressure to obtain a heavier products by distilling off the unreacted benzene (boiling point 80° C.), ethylbenzene (boiling point 136° C.) and polyethylbenzene (boiling point 176°–250° C.), respectively. The raw material fraction of the present invention can be obtained by distilling further the heavier product. While, the raw material fraction of the present invention can be obtained by directly distilling the alkylation products. Either method will do.

The boiling point of the raw material fraction of the present invention which is recovered by the above method must be in the range of 275°–305° C., preferably 285°–300° C. When the boiling point is above 305° C., the fraction contains PEPE as well as much 1,1-(4-ethylphenyl)phenylethane, which is a p-isomer of PEPE. If this 1,1-(4-ethylphenyl)phenylethane is treated in a succeeding dehydrogenation and hydroesterification steps, it is difficult to separate off the derivative of this compound. Accordingly, it is desirable that the boiling point of the raw material fraction of the present invention does not exceed 305° C. In the case that the boiling point is lower than 275° C., it is not desirable in that the treatment in the succeeding process is uneconomical because the PEPE content is lowered.

In the raw material fraction of the present invention, PEPE is contained in a high concentration, while the o-isomer of 1,1-(2-ethylphenyl)phenylethane is not contained substantially. However, besides PEPE, several impurities typically exemplified by polyalkylbenzenes including various isomers are contained in this fraction. With regard to these polyalkylbenzenes, accurate structural analysis is difficult and boiling points of some of them are close to that of PEPE, therefore, the separation of them from PEPE by means of any ordinary method is difficult. This is the reason why the effective use of PEPE in such a fraction has never been accomplished.

The dehydrogenation raw material fraction of the present invention which is prepared by the above described process is used for the above-mentioned dehydrogenation step (I) and then it is hydroesterified in the hydroesterification step (II).

α-(m-(1-Phenylethenyl)phenyl)propionic acid or its alkyl ester, that is the m-isomer of α-((1-phenylethenyl)phenyl)propionic acid obtained through the method of the invention, is easily converted into a medicine of ketoprofen (trade name) by oxidizing it by a conventional oxidation methods such as permanganate oxidation, hypochlorite oxidation, or oxidation by contact with molecular oxygen in the presence of an oxidation catalyst and, if necessary, hydrolyzing. It is possible that the hydrolysis is carried out prior to the oxidation.

According to the present invention, the diolefin having a vinyl group of (1-arylethenyl)vinylbenzene of the formula (I) is selectively hydroesterified. That is, only the vinyl group is hydroesterified to produce α-((1-arylethenyl)phenyl)propionic acid or its alkyl ester of the foregoing formula (II). While, the compound in which another internal olefinic double bond is hydroesterified, is not produced substantially.

The reaction product of the dehydrogenation step of (I) is recovered only by the industrial distillation operation and it is then fed to the next step (II) without any particular refining treatment. Even though the operation is not accompanied by severe refining, an aimed product in quite a high purity can be obtained in the present invention.

In general, it cannot be considered to utilize a raw material without refining treatment which contains side reaction products of structurally or physically resembling compounds. However, this has been made possible for the above described reason in the present invention.

Accordingly, the method of the present invention can provide the highest catalytic efficiency of dehydrogenation catalyst and it is economical and valuable in view of industry.

BEST MODE FOR CARRYING OUT THE INVENTION

The present invention is described in the following with reference to examples.

REFERENCE PREPARATION EXAMPLE 1

Synthesis of 1-(3-Vinylphenyl)-1-phenylethylene

To a 2 liter three-neck flask equipped with a dropping funnel, a reflux condenser and a stirrer was added 25.5 g (1.05 mole) of metallic magnesium and it was dried sufficiently by supplying dry nitrogen gas. After that, 50 ml of tetrahydrofuran which had been dried with a molecular sieve 5A, was put into the flask and the contents were stirred vigorously. A solution of 183 g (1.0 mole) of 3-vinylbenzene bromide in 500 ml of dried tetrahydrofuran was then dropped little by little over 2 hours. The reaction temperature was maintained 75° to 80° C. and, after the addition of the solution, the stirring was continued for further 1 hour as it stands. Into the thus obtained Grignard reagent of 3-vinylphenylmagnesium bromide, a solution of 122.6 g (1.02 mole) of acetophenone in 500 ml of dried tetrahydrofuran was dropped little by little over 2 hours. The reaction temperature was maintained at 75° to 80° C. and, after the dropping, the stirring was continued for further 1 hour as it stands. The reaction mixture was then poured into 3 liter of an aqueous solution of 75 g of ammonium chloride and it was left to stand still for 20 hours and an oily layer was recovered to obtain 1-(3-vinylphenyl)-1-phenylethyl alcohol in a yield of 89% (acetophenone basis) by distilling off the tetrahydrofuran.

To a 300 ml three-neck flask with a distillation column and a dropping funnel was added 81 g of potassium hydrogensulfate and the pressure was reduced to 15 to 20 mm Hg. The obtained alcohol was then dropped into the flask little by little over 2 hours. The water produced by dehydration and oily components were recovered from the top of the distillation column and 1-(3-vinylphenyl)-1-phenylethylene was obtained in a yield of 100% (on the basis of raw material alcohol) from the oily layer by a separatory funnel. The dehydration reaction was carried out at a temperature of 200° to 250° c.

The analytical data on the thus produced 1-(3-vinylphenyl)-1-phenylethylene (formula I) are shown in the following:

Boiling Point: 134.0°–135.5° C./2.0–3.0 mm Hg

IR: (Neat) cm$^{-1}$

-continued

| 3050, | 1690, | 1495, | 1260, | 995, | 900, |
|---|---|---|---|---|---|
| 810, | 780, | 700 | | | |

| $^1$H-NMR: (CCl$_4$, δ ppm) | |
|---|---|
| 7.10–7.70 | (9H Multiplet) |
| 6.65–6.80 | (1H Quadruplet) |
| 5.65–5.80 | (1H Doublet) |
| 5.45–5.50 | (2H Doublet) |
| 5.20–5.30 | (1H Doublet) |

| Elemental Analysis: (as C$_{16}$H$_{14}$) | |
|---|---|
| Calculated: | C: 93.20% |
| | H: 6.80% |
| Found: | C: 93.24% |
| | H: 6.76% |

EXAMPLE 1

Preparation of α-(3-(1-Phenylethenyl)phenyl)propionic Acid

To a 500 ml autoclave with a stirrer were added 43 g of 1-(3-vinylphenyl)-1-phenylethylene obtained in the above Example and 5.5 g of bisdichlorotriphenyl phosphine palladium, 80 g of 10% hydrochloric acid and 80 ml of toluene as a solvent. The pressure was raised up to 100 kg/cm$^2$ by carbon monoxide at room temperature and the pressure was then raised further to 300 kg/cm$^2$ with raising temperature up to 120° C. After the absorption of carbon monoxide by reaction was ceased, the reaction was further continued for 24 hours.

After the reaction, the autoclave was cooled to recover the reaction mixture and an oily layer and an aqueous layer were separated by a separatory funnel. The oily layer was subjected to three times of extraction with 50 ml of 8% sodium hydroxide aqueous solution. After separating the extracted aqueous solution, it was combined with the aqueous layer and pH was made to 2 by adding hydrochloric acid. After that, it was extracted three times with 500 ml of chloroform and the chloroform was distilled off under reduced pressure from the extract to obtain 44.7 g of the compound of the above title. The analytical results of the compound are shown in the following. According to the analysis, the compound in which the ethynylidene-type double bond of internal olefin was hydroesterified, was not substantially observed.

Property: Melting Point: 69.0°–71.0° C.

| IR: (Neat) cm$^{-1}$ | | | | | |
|---|---|---|---|---|---|
| 3030, | 2750, | 2650, | 1715, | 1610, | 1420, |
| 1240, | 1070, | 910, | 785, | 710 | |

| $^1$H-NMR: (CCl$_4$, δ ppm) | |
|---|---|
| 12.20 | (1H Singlet) |
| 6.80–7.50 | (9H Multiplet) |
| 5.38 | (2H Singlet) |
| 3.45–3.90 | (1H Quadruplet) |
| 1.35–1.65 | (3H Doublet) |

| Elemental Analysis: (as C$_{17}$H$_{16}$O$_2$) | |
|---|---|
| Calculated: | C: 80.95% |
| | H: 6.35% |
| | O: 12.70% |
| Found: | C: 80.91% |
| | H: 6.32% |
| | O: 12.77% |

EXAMPLE 2

Preparation of α-(3-(1-Phenylethenyl)phenyl)propionic Acid Methyl Ester

To a 500 ml autoclave with a stirrer were added 43 g of 1-(3-vinylphenyl)-1-phenylethylene obtained in the above Example, 0.74 g of palladium chloride (II), 2.19 g of triphenyl phosphine, 13.4 g of methyl alcohol and 90 ml of toluene as a solvent. The pressure was raised up to 150 kg/cm$^2$ by carbon monoxide at room temperature and then the temperature was raised to 125° C. by heating and the pressure was simultaneously raised to 400 kg/cm$^2$ with raising temperature. After the absorption of carbon monoxide was ceased, the reaction was further continued for 16 hours. After the reaction, the reaction mixture was distilled under reduced pressure of 2–3 mm Hg to obtain α-(3-(1-phenylethenyl)phenyl)-propionic acid methyl ester of 144.5°–145.5° C. in boiling point in a yield of 87% (on the basis of 1-(3-vinylphenyl)-1-phenylethylene). The results of spectrum analysis are shown in the following. According to the analysis, the compound in which the ethynylidene-type double bond of internal olefin was hydroesterified, was not substantially observed.

| IR: (Neat) cm$^{-1}$ | | | | | |
|---|---|---|---|---|---|
| 3040, | 2995, | 2960, | 2880, | 2850, | 1740, |
| 1610, | 1500, | 1445, | 1340, | 1260, | 1190, |
| 1075, | 1032, | 905, | 785, | 710 | |

| $^1$H-NMR: (CCl$_4$, δ ppm) | |
|---|---|
| 6.70–7.30 | (9H Multiplet) |
| 5.32 | (2H Singlet) |
| 3.20–3.75 | (4H Multiplet) |
| 1.45–1.56 | (3H Doublet) |

| Elemental Analysis: (as C$_{18}$H$_{18}$O$_2$) | |
|---|---|
| Calculated: | C: 81.20% |
| | H: 6.77% |
| | O: 12.03% |
| Found: | C: 81.20% |
| | H: 6.80% |
| | O: 12.00% |

EXAMPLE 3

Preparation of α-(3-(1-Phenylethenyl)phenyl)propionic Acid tert-Butyl Ester

In the like manner as Example 2, 1-(3-vinylphenyl)-1-phenylethylene was hydroesterified with tert-butyl alcohol. The yield of obtained α-(3-(1-phenylethenyl)-phenyl)propionic acid tert-butyl ester was 50% on the basis of the starting olefin. The results of analysis on the entitled α-(3-(1-phenylethenyl)phenyl)propionic acid tert-butyl ester are shown in the following. According to the analysis, the compound in which the ethynylidene-type double bond of internal olefin was hydroesterified, was not substantially observed.

Boiling Point: 172°–174° C./2–3 mm Hg

| IR: (Neat) cm$^{-1}$ | | | | | |
|---|---|---|---|---|---|
| 3045, | 2990, | 2955, | 1745, | 1490, | 1370, |
| 1260, | 1150, | 915, | 875, | 820, | 775, |
| 715 | | | | | |

| $^1$H-NMR: (CCl$_4$, δ ppm) | |
|---|---|
| 6.75–7.30 | (9H Multiplet) |
| 5.32 | (2H Singlet) |
| 3.50 | (1H Quadruplet) |

-continued

| 1.58 | (9H Singlet) |
| --- | --- |
| 1.41–1.53 | (3H Doublet) |

| Elemental Analysis: (as $C_{21}H_{24}O_2$) | |
| --- | --- |
| Calculated: | C: 81.82% |
| | H: 7.79% |
| | O: 10.39% |
| Found: | C: 81.80% |
| | H: 7.80% |
| | O: 10.40% |

EXAMPLE 4

Step (I) Dehydrogenation of 1-Phenyl-1-ethylphenyl-ethane

An iron oxide dehydrogenation catalyst of G-64C (trade mark) made by Nissan Girdler Catalysts Co., Ltd. of 15 to 25 mesh in particle size was used. To a reaction tube of 560° C. were continuously fed 10 ml/hr of a fraction of 1-phenyl-1-ethylphenyl-ethane having a boiling range of 285° C. to 295° C. (atmospheric pressure basis) and 100 ml/hr of water, and the outlet of the reaction tube was cooled. The oily layer obtained after separation and settling was analyzed by gas chromatography. The analytical results on the oily layer which was obtained from 4 hours to 76 hours after the start of reaction are shown in the following.

TABLE 1

| Results of Analysis | |
| --- | --- |
| Components | Analytical Value (%) |
| Light Fraction | 2.7 |
| 1,1-Diphenylethane | 0.6 |
| 1-m-Ethylphenyl-1-phenylethane | 19.0 |
| 1-m-Vinylphenyl-1-phenylethane | 2.1 |
| 1-m-Ethylphenyl-1-phenylethylene | 32.9 |
| 1-m-Vinylphenyl-1-phenylethylene | 41.1 |
| Heavy Fraction | 1.6 |
| Total | 100.0 |

EXAMPLE 5

Dehydrogenation of 1-phenyl-1-ethylphenyl-ethane was carried out in the like manner as in Example 4 except that a chromium oxide/iron oxide dehydrogenation catalyst of G-64A (trade mark) made by Nissan Girdler Catalysts Co., Ltd. was used.

Oily layer was recovered from 4 hours to 12 hours after the start of reaction, results of gas chromatographic analysis of which are shown in the following.

TABLE 2

| Results of Analysis | |
| --- | --- |
| Components | Analytical Value (%) |
| Light Fraction | 3.1 |
| 1,1-Diphenylethane | 0.8 |
| 1-m-Ethylphenyl-1-phenylethane | 23.6 |
| 1-m-Vinylphenyl-1-phenylethane | 1.3 |
| 1-m-Ethylphenyl-1-phenylethylene | 37.1 |
| 1-m-Vinylphenyl-1-phenylethylene | 32.2 |
| Heavy Fraction | 1.9 |
| Total | 100.0 |

EXAMPLE 6

Dehydrogenation of 1-phenyl-1-ethylphenyl-ethane was carried out in the like manner as in Example 4 except the conditions shown in the following Table 3. The results of tests are shown also in Table 3.

TABLE 3

| Number | 6a | 6b | 6c | 6d | 6e |
| --- | --- | --- | --- | --- | --- |
| 1-m-Ethylphenyl-1-phenylethane (ml/h) | 10 | 20 | 40 | 10 | 10 |
| Diluent | Nitrogen | Water | Water | Water | Water |
| Do., Feed Qty. (ml/hr) | 2000 | 200 | 200 | 100 | 100 |
| Reaction Temper. (°C.) | 560 | 600 | 600 | 450 | 500 |
| Analytical Results (%) | | | | | |
| Light Fraction | 3.4 | 4.4 | 1.9 | 0.8 | 1.4 |
| 1,1-Diphenylethane | 0.6 | 0.7 | 0.2 | 0.1 | 0.4 |
| 1-m-Ethylphenyl-1-phenylethane | 20.6 | 25.7 | 30.6 | 73.9 | 58.5 |
| 1-m-Vinylphenyl-1-phenylethane | 1.6 | 1.8 | 1.7 | 1.2 | 1.4 |
| 1-m-Ethylphenyl-1-phenylethylene | 33.3 | 33.4 | 39.4 | 15.6 | 27.8 |
| 1-m-Vinylphenyl-1-phenylethylene | 37.7 | 30.3 | 23.8 | 7.8 | 9.4 |
| Heavy Fraction | 2.8 | 3.7 | 2.4 | 0.6 | 1.1 |

EXAMPLE 7

Step (II) Hydroesterification

The reaction product obtained in Example 4 was distilled at a reduced pressure of 2 mm Hg to 3 mm Hg by an ordinary distillation apparatus to obtain a dehydrogenation product of a fraction having a distilling temperature of 100° C. to 150° C. (recovery rate 94%). This fraction was subjected to hydroesterification.

To a 500 ml autoclave with a stirrer were added 100 g of the above fraction, 20 g of methyl alcohol, 170 mg of palladium chloride and 0.5 g of triphenylphosphine. The pressure was maintained at 90 kg/cm$^2$ by carbon monoxide and the reaction was continued for 12 hours at 120° C. After the reaction, the reaction mixture was cooled and unreacted gas was discharged. Then, 54.2 g of a fraction (a) of a distilling temperature of 120° C. to 138° C. at a reduced pressure of 2 mm Hg to 3 mm Hg and 52.3 g of a fraction (b) of a distilling temperature of 142° C. to 148° C. were obtained by reduced pressure distillation.

The composition of the fraction (a) was 37.8% of 1-m-ethylphenyl-1-phenylethane and 59.2% of 1-m-ethylphenyl-1-phenylethylene. It could be confirmed that the dehydrogenation product of the step (I) of 1-phenyl-1-(m-ethylphenylethylene did not reacted in the hydroesterification of the step (II).

The composition of the fraction (b) was m-(1-phenylethenyl)phenyl]propionic acid methyl ester of 96.8% in purity and the ratio in α-aryl compound/β-aryl compound was 15.7. Furthermore, in [m-(1-phenylethenyl)phenyl]propionic acid methyl ester, the double bond in the ethylene moiety having two phenyl groups was maintained and only the ethylene moiety having one phenyl group was hydroesterified.

EXAMPLE 8

The reaction product obtained in the step (I) was hydroesterified in the like manner as Example 7 except that 0.68 g of dichloropalladium bistriphenylphosphine and 0.3 g of triphenylphosphine were used as hydroesterification catalysts.

The composition and recovery rate of fraction (a) obtained by reduced pressure distillation were the same as those in Example 7. According to analysis, the fraction (b) was [m-(1-phenylethenyl)phenyl]propionic acid methyl ester of 94 7% in purity and the ratio in α-aryl compound/β-aryl compound was 18.9, and only the ethylene moiety having one phenyl group was hydroesterified.

EXAMPLE 9

Hydroesterification was carried out in the like manner as in Example 7 except that 40 g of sec-butyl alcohol was used in place of methyl alcohol.

The fraction of 138° to 148° C. in distilling temperature obtained by reduced pressure distillation at 0.5 mm Hg to 1 mm Hg was [m-(1-phenylethenyl)phenyl]propionic acid sec-butyl ester. Like the fractions (b) obtained in Examples 7 and 8, the ethylene moiety having 2 phenyl group was not hydroesterified and the double bond was maintained intact.

REFERENCE EXAMPLE

Preparation of Ketoprofen by Oxidation and Hydrolysis of Methyl Ester

The fraction (b) obtained in Example 7 was subjected to precision fractional distillation to obtain α-]3-(1-phenylethenyl)phenyl]propionic acid methyl ester of 125° C. to 130° C. in distilling temperature at a reduced pressure of 0.5 mm Hg to 1 mm Hg (purity 98.3% and ratio in α-aryl compound/β-aryl compound 72).

The above fraction (36 g) was dissolved in 250 ml of benzene and 250 ml of water was added and it was then stirred vigorously into suspension. With maintaining the suspended state, 2 liter of 2% potassium permanganate aqueous solution was slowly dropped in 2 hours. The stirring was continued also after the dropping to allow it to react for 18 hours.

After the reaction, it was acidified by adding concentrated sulfuric acid and 35 g of sodium sulfite was added. By adding further 500 ml, it was extracted three times with 150 ml of ether. After washing the ether solution with water, the ether was evaporated off under reduced pressure and it was maintained at reflux temperature after adding 5% sodium hydroxide aqueous solution.

After cooling, it was acidified by adding hydrochloric acid and the aqueous layer was extracted with ether The ether was evaporated off and the obtained solid material was recrystallized with a benzene/petroleum ether mixture to obtain 23 g of α-(m-benzoylphenyl)-propionic acid (antiphlogistic agent, trade name: ketoprofen). The melting point and the spectrum of the product were the same as those of an authentic sample.

With regard to the alkyl esters in Examples 8 and 9, it was confirmed that ketoprofen can be obtained by oxidizing and hydrolyzing likewise.

EXAMPLE 10

Benzene and ethylene in a molar ratio of 9:1 were allowed to contact together for 1 hour in liquid phase with stirring in a reaction vessel at a temperature of 130° C. and a pressure of 4.9 kg/cm$^2$ in the presence of aluminum chloride. The duration of 1 hour was sufficient for adding the whole ethylene. The use quantity of aluminum chloride was 0.0034 part by weight relative to the produced ethylbenzene. As a result of the analysis of the obtained alkylation product, it was understood that 49.0% by weight of benzene, 32.9% by weight of ethylbenzene, 17.5% by weight of polyethylbenzene and 0.5% by weight of heavier product were contained. Unreacted benzene, ethylbenzene and polyethylbenzene were recovered by distilling this alkylation product to obtain the heavier product which was 0.014 part by weight relative to the produced ethylbenzene. This heavier product was further subjected to distillation to obtain a fraction of a boiling range of 280°–305° C. (as atmospheric pressure). As a result of analysis of this product, it was understood that it was 82% of PEPE and 18% of impurity mainly containing polyalkylbenzene.

The obtained fraction (124 g) was then subjected to dehydrogenation and hydroesterification according to Example 4 and Example 7.

As a result, α-(m-(1-phenylethenyl)phenyl)propionic acid methyl ester as a fraction of 142°–148° C. in distilling temperature of at 2–3 mm Hg in a yield of 34% (PEPE basis) was obtained (purity 96.8%, ratio in α-aryl compound/β-aryl compound 15.7).

With regard to this material, it was confirmed that, by oxidizing and hydrolyzing like the foregoing Reference Example, ketoprofen which was the same as the authentic sample could be obtained.

We claim:

1. A process for selective hydroesterification which is characterized in the step of reacting a (1-arylethenyl)vinylbenzene represented by the following formula (I) with carbon monoxide and water or a lower alcohol in the presence of a noble metal complex carbonylation catalyst at a temperature of 40° to 200° C. and a carbon monoxide pressure of 20 to 700 kg/cm$^2$, thereby producing α-((1-arylethenyl)phenyl)propionic acid or its alkyl ester represented by the following formula (II),

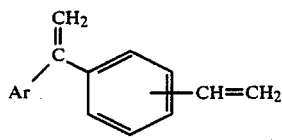
Formula (I)

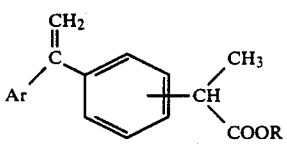
Formula (II)

(in which Ar is a substituted aryl group which may have a substituent group other than vinyl group and R is a hydrogen atom or a lower alkyl group).

2. The process for selective hydroesterification in claim 1, wherein 3-(1-phenylethenyl)vinylbenzene of said formula (I) is reacted to produce α-(3-(1-phenylethenyl)phenyl)propionic acid or its ester.

3. The process in claim 1, wherein (1-arylethenyl)vinylbenzene of said formula (I) is a mixture with 1,1-di(-substituted aryl)ethylenes represented by the following formula (III),

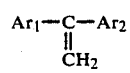
(III)

in which Ar$_1$ and Ar$_2$ are the same or different substituted aryl groups and their substituent groups may be replaced by groups other than vinyl group.

4. The process in claim 3, wherein said 1,1-di(substituted aryl)ethylene of the formula (III) is 1-phenyl-1-ethylphenylethylene.

5. The process in claim 3, which comprises the following Step (I) and Step (II), Step (I):

1-phenyl-1-ethylphenyl-ethane represented by the formula (A) is brought into contact with iron oxide and/or chromium oxide dehydrogenation catalyst at a temperature of 400° C. to 650° C. in the presence of an inert gas to obtain a dehydrogenation product containing at least 1-phenyl-1-ethylphenyl-ethylene represented by the formula (B) and 1-phenyl-1-vinylphenyl-ethylene represented by the formula (C), and Step (II):

the dehydrogenation product obtained in the Step (I) containing at least 1-phenyl-1-ethylphenyl-ethylene represented by the formula (B) and 1-phenyl-1-vinylphenyl-ethylene represented by the formula (C) is hydroesterified with carbon monoxide and water or a lower alcohol having 1 to 4 carbon atoms in the presence of a noble metal complex carbonylation catalyst, at a reaction temperature of 40°–200° C. and a reaction pressure of 20–700 kg/cm².

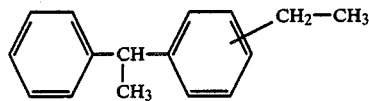

Formula (A)

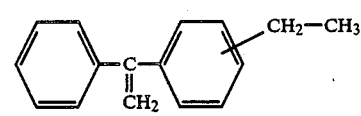

Formula (B)

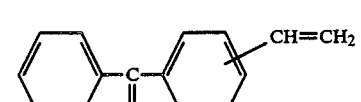

Formula (C)

6. The process in claim 5, wherein said 1-phenyl-1-ethylphenyl-ethane is a fraction containing 1-phenyl-1-ethylphenyl-ethane which is recovered from the heavy by-product fraction in the preparation of ethylbenzene by alkylating benzene with ethylene.

7. The process in claim 6, wherein the catalyst used for alkylation is aluminum chloride or synthetic zeolite catalyst.

8. The process in claim 1, wherein the noble metal in said noble metal complex catalyst is selected from Pd, Rh and Ir.

* * * * *